(12) United States Patent
Festag

(10) Patent No.: US 12,070,423 B2
(45) Date of Patent: *Aug. 27, 2024

(54) OPHTHALMOLOGICAL LASER THERAPY SYSTEM

(71) Applicant: Carl Zeiss Meditec AG, Jena (DE)

(72) Inventor: Karsten Festag, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 444 days.

This patent is subject to a terminal disclaimer.

(21) Appl. No.: 17/369,870

(22) Filed: Jul. 7, 2021

(65) Prior Publication Data
US 2021/0330500 A1    Oct. 28, 2021

Related U.S. Application Data

(63) Continuation of application No. 16/080,607, filed as application No. PCT/EP2017/055377 on Mar. 8, 2017, now Pat. No. 11,071,649.

(30) Foreign Application Priority Data

Mar. 11, 2016  (DE) .......................... 102016204032.4

(51) Int. Cl.
   *A61F 9/008*   (2006.01)
(52) U.S. Cl.
   CPC .......... *A61F 9/00825* (2013.01); *A61F 9/008* (2013.01); *A61F 9/00802* (2013.01);
   (Continued)
(58) Field of Classification Search
   CPC .. A61F 9/008; A61F 9/00825; A61F 9/00802; A61F 9/00821
   See application file for complete search history.

(56) References Cited

U.S. PATENT DOCUMENTS

| 8,771,262 B2 | 7/2014 | Rathjen |
| 11,071,649 B2 * | 7/2021 | Festag ................ A61F 9/00825 |

(Continued)

FOREIGN PATENT DOCUMENTS

| CN | 101080206 A | 11/2007 |
| CN | 101626743 A | 1/2010 |

(Continued)

OTHER PUBLICATIONS

PCT International Search Report and Written Opinion for International Application No. PCT/EP2017/055377, mailed Jun. 6, 2017, 16 pages.

(Continued)

*Primary Examiner* — Joseph M Dietrich
(74) *Attorney, Agent, or Firm* — DeWitt LLP

(57) ABSTRACT

An ophthalmological laser therapy system having an appliance base and an appliance head, displaceable relative to one another by translational movement and having a laser device and to a corresponding method. A laser pivot arm is fastened to the appliance head pivotable about a horizontal first axis. The laser pivot arm is encompassed by a pivot arm housing, which is fastened in a separately pivotable manner on the appliance head in coaxial fashion relative to the laser pivot arm and/or by virtue of an examination pivot arm with an examination device, defining an examination volume, being fastened to the appliance head pivotable about a second axis, wherein both axes are arranged such that a work volume of a laser beam, when the laser pivot arm is in a work position, is a partial volume of the examination volume, when the examination pivot arm is in a work position.

18 Claims, 8 Drawing Sheets

(52) U.S. Cl.
CPC . *A61F 9/00821* (2013.01); *A61F 2009/00851* (2013.01); *A61F 2009/0087* (2013.01); *A61F 2009/00872* (2013.01); *A61F 2009/00887* (2013.01)

(56) References Cited

U.S. PATENT DOCUMENTS

| | | |
|---|---|---|
| 2010/0042081 A1 | 2/2010 | Rathjen |
| 2013/0085483 A1 | 4/2013 | Rathjen |
| 2014/0046308 A1 | 2/2014 | Bischoff et al. |
| 2014/0107634 A1 | 4/2014 | Vogler |
| 2017/0340483 A1 | 11/2017 | Rill |

FOREIGN PATENT DOCUMENTS

| | | |
|---|---|---|
| CN | 102014732 A | 4/2011 |
| CN | 102076290 A | 5/2011 |
| CN | 202386950 U | 8/2012 |
| CN | 103648449 A | 3/2014 |
| CN | 104814828 A | 8/2015 |
| DE | 10 2011 116369 | 4/2013 |
| WO | WO 2006/102971 A2 | 10/2006 |
| WO | WO2010102804 | 9/2010 |
| WO | WO 2012/152496 A1 | 11/2012 |

OTHER PUBLICATIONS

English translation of International Search Report for International Application No. PCT/EP2017/055377, mailed Jun. 6, 2017, 2 pages.
DE Search Report for 10 2016 204 032.4, dated Oct. 26, 2016, 9 pages.
English translation of International Report on Patentability for PCT International Search Report and Written Opinion for International Application No. PCT/EP2017/055377, mailed Sep. 20, 2018, 8 pages.
Application and File History for U.S. Appl. No. 16/080,607, filed Aug. 28, 2018. Inventor Karsten Festag.

\* cited by examiner

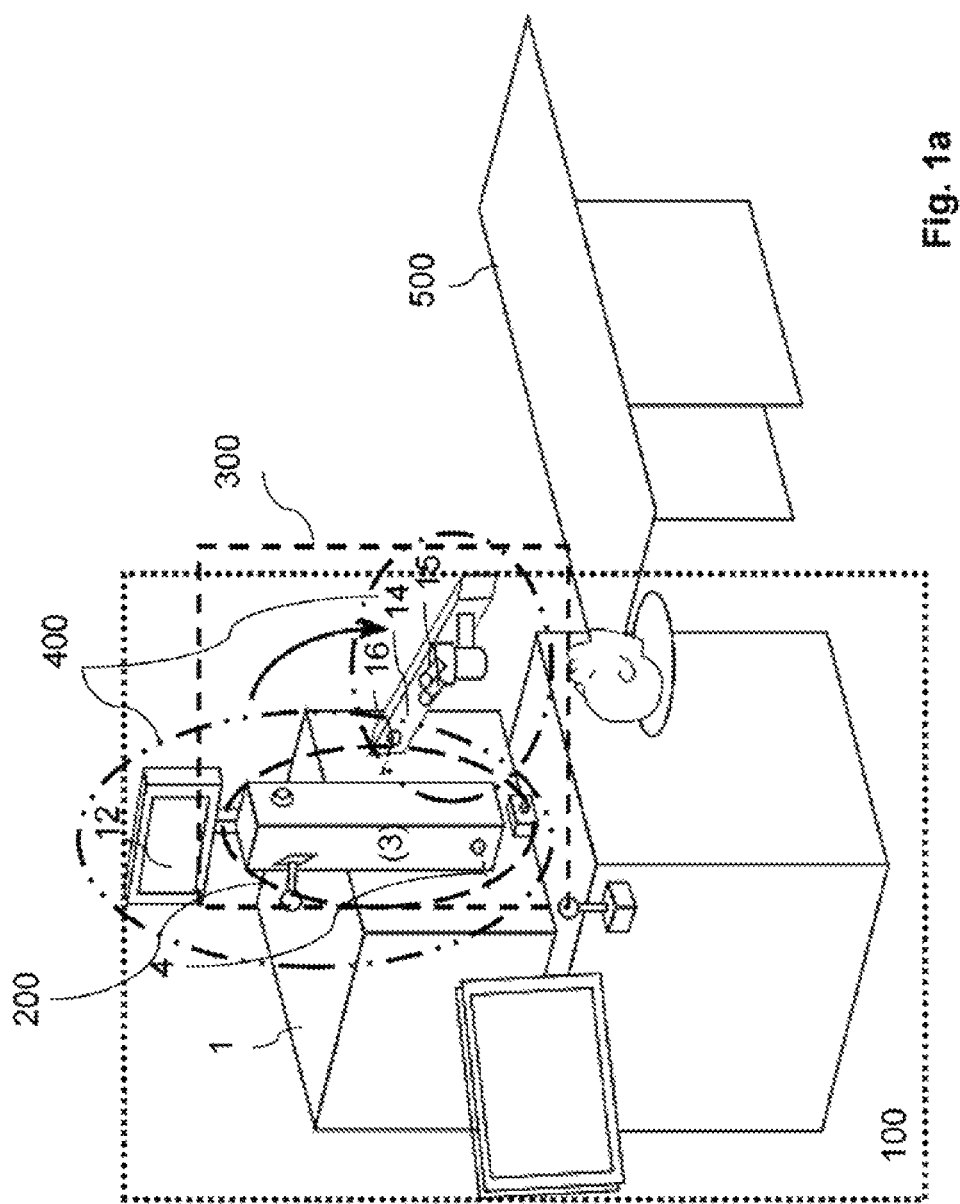

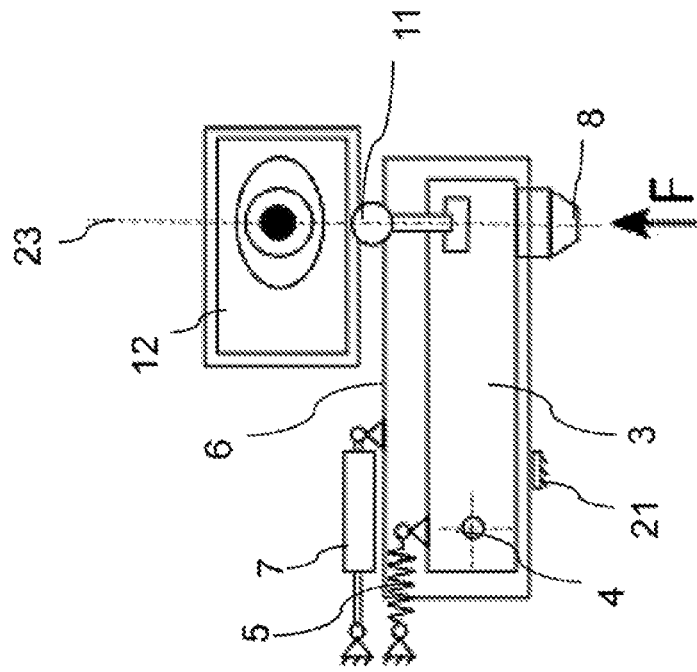
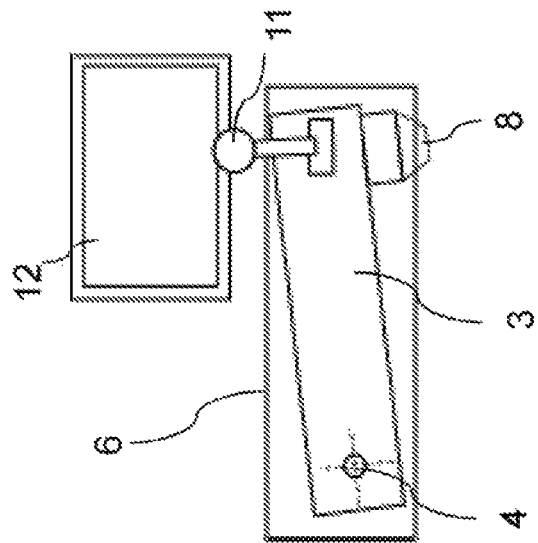
Fig. 2a
Fig. 2b

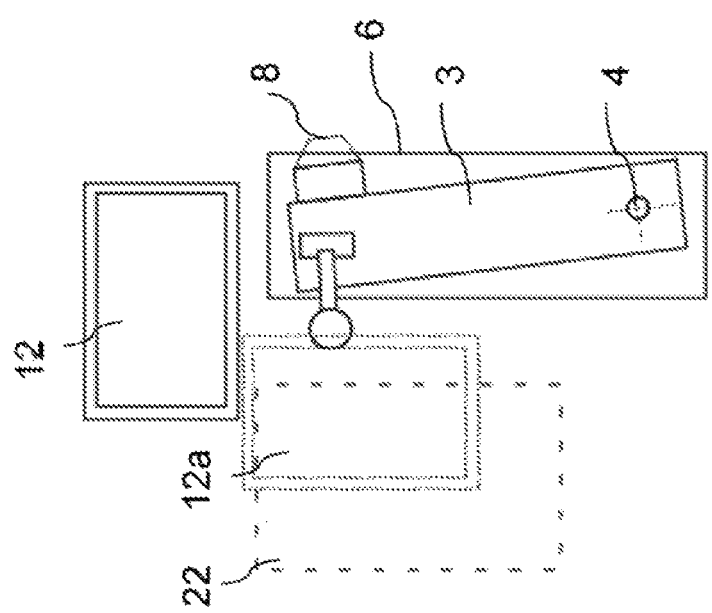

OPHTHALMOLOGICAL LASER THERAPY SYSTEM

RELATED APPLICATIONS

This application is a continuation of application Ser. No. 16/080,607, filed Aug. 28, 2018, entitled "Ophthalmological Laser Therapy System," which in turn is a National Phase entry of PCT Application No. PCT/EP2017/055377, filed Mar. 8, 2017, which claims the benefit of priority to German Application No. 10 2016 204 032.4, filed Mar. 11, 2016, each of which is hereby fully incorporated herein by reference.

TECHNICAL FIELD

The present invention relates to an ophthalmological laser therapy system having an appliance base and an appliance head, which are displaceable in relation to one another by a translational movement, and having a laser device that contains a laser source and a first laser therapy optical unit and a laser pivot arm with a second laser therapy optical unit and a laser exit aperture. Furthermore, the present invention relates to a corresponding ophthalmological laser therapy method.

BACKGROUND

By now, the combination of a laser therapy apparatus for producing cuts in an eye tissue, or for ablating or coagulating eye tissue by application of laser radiation, with an examination apparatus is conventional in ophthalmological laser therapy—either by way of integration in a common system or by installing the examination apparatus in the spatial vicinity of the laser therapy apparatus in order to facilitate a change between the two apparatuses without having to move the patient into another room.

By way of example, this is very advantageous in laser-assisted eye surgery for correcting refractive errors or for the therapy of other eye disorders such as e.g. a cataract by cataract surgery, where work steps for characterizing the eye structures alternate with surgical steps and steps for verifying the surgical intervention or for assisting the surgical intervention. Thus, the eye structures can be initially characterized by application of optical coherence tomography (OCT) or of ultrasound. Hereafter, eye tissue can be cut by application of a pulsed laser beam, i.e., separated by photodisruption in this case. The result can then be verified by a surgical microscope and subsequent steps, such as e.g., suctioning away of a cloudy eyes lens previously cut by the laser beam and/or comminuted by ultrasound in cataract surgery, can be performed with monitoring by the surgical microscope.

In the case of refractive error corrections, too, such as e.g. for performing a "SMILE" treatment, i.e. a lenticule extraction by a small incision ("small incision lenticule extraction"), two main work steps should be performed after preparing the patient and after an appropriate characterization of the eye structures: firstly, the laser therapy, in which the patient's eye is contacted to the laser optical unit by a contact glass and laser cuts are implemented in the eye, and, secondly, the lenticule extraction, in which the surgeon removes the lenticule that was cut during the laser therapy with monitoring by a surgical microscope.

A similar statement applies for implantations of lenticules in the patient's eye: Here, a corresponding receptacle region in the eye tissue, generally in the corneal tissue of the eye, is initially created in a laser-assisted manner by separating this eye tissue and an implant is subsequently introduced into the receptacle region and adapted, with monitoring by a surgical microscope, for example.

Using currently conventional methods, these work steps are carried out at spatially separated positions. By way of example, the laser therapy position is approximately 200 mm behind and approximately 100 mm above the lenticule extraction position during the "SMILE" treatment by application of the "VisuMax".

Thus, with the aid of ophthalmological laser therapy systems according to the prior art, the relative position between the respective treatment apparatus and the patient must be significantly modified between the various work steps. This repositioning over a long path leads to three substantial disadvantages:

It requires great technical outlay for realizing a large range of movement. It moreover requires much space—both for the installation space of the ophthalmological laser therapy system and for the region to be kept clear for the movement. The method duration is relatively long because a relatively long time for repositioning is required between the work steps as the displacement speed during repositioning is low for safety reasons.

According to the prior art, the required mobility for repositioning the patient or the patient's eye can be provided in the patient bearing device. It can likewise be present in the required systems, i.e., the laser device and the examination devices: the spatial requirements to this end are huge particularly in the case of non-integrated systems.

A further great disadvantage of the known appliances lies in the restriction of the free space for the access and exit of the patient as a result of the laser optical unit that, as a rule, is situated over the patient bearing device. To this end, document WO 2012/152496 A1 has published a method in which the laser therapy optical unit is pivoted upward by 90° and received in the housing of the base appliance. However, this embodiment is disadvantageous in that the laser therapy optical unit is relatively unprotected in its work position from external mechanical influences.

SUMMARY

Embodiments of the present invention describe an ophthalmological laser therapy system and a corresponding method, which allow working in the smallest possible space and without repositioning of the patient but nevertheless effectively protect the sensitive laser therapy optical unit, in particular a pivotable laser therapy optical unit.

Many of the above discussed problems are solved by an ophthalmological laser therapy system that is configured to carry out all work steps of laser therapy on the eye of a patient in such a way that the point of action of all work steps remains fixed while there is maximum work freedom for a surgeon, i.e., the position of the patient's eye need not be modified during the entire laser therapy. The position of the patient's eye in the first work step determines the position of the patient's eye in all subsequent work steps and hence the point of action of the devices required in each case.

Here, an ophthalmological laser therapy should be understood to mean any therapy in which a laser beam is focused into the tissue of an eye in such a way that it modifies the tissue. In particular, the ophthalmological laser therapy contains corresponding surgical interventions, in which a tissue of the eye is "cut" by photodisruption by application of a laser, such as a pulsed laser such as a femtosecond laser, for example, in which a region of an eye tissue is ablated by an ablation effect or in which eye tissue is "adhesively bonded" to itself by a coagulation effect, or in which the refractive index of the material, i.e., of an eye tissue or else an implant, is modified by the laser radiation.

In particular, an example embodiment of the invention includes an ophthalmological laser therapy system comprising an appliance base, an appliance head, a laser device and a laser pivot arm.

While the appliance base represents the base of the ophthalmological laser therapy system that is immovable during a laser therapy method—including the preparing and post-processing work steps—, the appliance head serves, in particular, for fastening movable superstructures. Moreover, it is, in turn, the basis for the common displacement of these superstructures in space. To this end, the appliance head is displaceable on the appliance base in at least an xy-plane by a translational movement. Here, the xy-plane is a plane that extends parallel to a stand plane or floor plane of the ophthalmological laser therapy system. Here, the ophthalmological laser therapy system is for example configured in such a way that a translational movement in the xy-plane can be carried out in any direction.

The ophthalmological laser therapy system as a whole can be fixedly installed on this stand plane in the process, or else it may comprise a transportation option such as a roller system, for example, which renders it possible to bring the system into a parked position before or after a corresponding laser therapy method.

The laser device contains a laser source and a first laser therapy optical unit, which are for example arranged in the appliance head. The power supply of the laser device and of the electronics, too, is for example arranged in the appliance base. The laser source is for example configured to produce pulsed laser radiation. In particular, a femtosecond laser source can be used here. Such a femtosecond laser source for example produces pulses to this end with a pulse duration of 100 fs to 600 fs with a pulse repetition rate of between 100 kHz and 100 MHz, for example from 500 kHz to 5 MHz, and a pulse energy from 20 nJ to 20 µJ, for example 100 nJ to 1 µJ.

The laser beam is transmitted through the first laser therapy optical unit into a laser pivot arm with a second laser therapy optical unit and a laser exit aperture.

Here, the laser exit aperture is the location at which a laser beam, in particular a therapy laser beam, emerges from the ophthalmological laser therapy system in order subsequently to reach its point of action, for example in a tissue of the eye. Here, the eye of a patient can be affixed to the laser exit aperture by a patient interface or a contact glass in order to establish a defined spatial relationship of the tissue to be treated in relation to the laser exit aperture.

The term laser therapy optical unit, which includes a first laser therapy optical unit, which is generally housed in the appliance head, and a second laser therapy optical unit in the laser pivot arm, should also include beam guiding structures here in addition to optical imaging elements such as fixed and/or movable lenses or lens systems. These beam guiding structures can be fixed and/or movable beam guiding structures. Here, movable beam guiding structures also contain appropriate scan systems. Galvanometer scanners, which can position the laser beam in a plane perpendicular to the beam axis by application of rotatable mirrors, are conventional. It is however also possible to displace a lens across the optical axis by application of a linear drive. One or more lenses are usually moved in the beam direction by application of a linear drive in order to change the depth offset of the focus. Linear drives to this end can be, e.g., a servomotor with a spindle, a piezo-drive or a moving-coil or moving-magnet drive.

Thus, the laser therapy optical unit serves to steer and form the laser beam from its emergence from the laser source up to its point of action, generally the tissue of an eye. In particular, it moreover serves for the corresponding desired displacement of the laser beam according to a planned scan pattern during a laser therapy step.

In principle, it is possible here to use an optical concept as described in WO 2006/102971 A2, for example. Therefore, the content of WO 2006/102971 A2, in the entirety thereof, is incorporated into the disclosure as a constituent part.

Here, the laser pivot arm is attached to the appliance head in a manner pivotable about a first axis. This first axis is for example a horizontal axis, i.e., an axis that extends parallel to the xy-plane.

In particular, the laser pivot arm is pivotable between a rest position and a work position, with the rest position representing a position in which the laser pivot arm is "stowed" in order to provide maximum work freedom for the surgeon or else for further devices during work steps in which no laser beam is required. Thus, as a rule, the rest position is a position in which the laser pivot arm is pivoted perpendicularly upward. By contrast, the work position is a position in which the laser pivot arm is brought into a for example horizontal position over the patient.

Here, various further work positions of the laser pivot arm are facilitated in addition to the horizontal work position in one configuration of this ophthalmological laser therapy system: To this end, the first and second laser therapy optical unit is appropriately configured in this configuration. To this end, it contains an arrangement of optical elements or scan elements in such a way that the guidance of the laser beam through the laser pivot arm is adaptable to the desired work position of the laser pivot arm. By way of example, this can be realized by pivotable mirrors instead of fixed mirrors, both at the entry into the second laser therapy optical unit, i.e., the optical unit of the laser pivot arm, and in front of the laser exit aperture.

Work position and rest position can be embodied as two end positions, which are optionally clearly identifiable by way of a stop.

Hence, as a rule, the laser pivot arm is an arm that is pivotable about an axis on the appliance head but which otherwise has a rigid embodiment, i.e., has no further pivot axes. A movement in space is possible by combining the pivot movement of the laser pivot arm about this first axis with a transversal movement in an xy-plane.

Moreover, a control unit ensures the control of the ophthalmological laser therapy system, in particular the translation movement of the appliance head on the appliance base and the pivot movement of the laser pivot arm, and the laser device. Controlling the laser device includes, in particular, controlling the production of a laser beam, appropriate steering of the laser beam by application of movable beam guiding application and hence controlling a scan movement of the focus of the laser beam. Here, the control unit also can comprise a plurality of control devices that are spatially separated from one another.

In a fundamental example embodiment, the ophthalmological laser therapy system according to the invention is characterized in that the laser pivot arm, with its second laser therapy optical unit and the laser exit aperture, is encompassed by a pivot arm housing, which is fastened in a separately pivotable manner on the appliance head in coaxial fashion relative to the laser pivot arm. Thus, laser pivot arm and pivot arm housing use the same pivot axis, albeit independently of one another.

Hence, the second laser therapy optical unit and the laser exit aperture adjoining this are surrounded by the pivot arm housing in a protective manner. Here, an appropriate opening in the pivot arm housing for the emergence point or the emergence region of the laser beam is provided for the laser exit aperture.

Expressed differently, the pivot arm housing forms an outer sleeve for the laser pivot arm that, however, is mounted separate from and coaxially with the laser pivot arm. As a rule, the laser pivot arm and pivot arm housing are pivoted simultaneously about their respective axes if the goal is to move the laser pivot arm in its pivot arm housing from a rest position (also referred to as a standby position) into its work position. Thus, this embodiment represents a true "arm-in-arm" solution.

Here, for example, the laser pivot arm is pivotable by a greater angle than the pivot arm housing. This allows the optical unit to be retracted into the pivot arm housing.

Beyond the common pivoting of the laser pivot arm and pivot arm housing, for example from the work position into the rest position or vice versa, this therefore initially allows the laser pivot arm to be "retracted" into or "engulfed" further in the pivot arm housing in order to provide it with additional protection during the movement, and also in its rest position or, in certain situations, in its work position. On the other hand, the laser pivot arm can be "extended" slightly further out of the pivot arm housing in order, for example, to make the coupling process of the patient's eye to the ophthalmological laser therapy system by use of a contact glass or patient interface easier. For this purpose, the laser pivot arm can be pivoted beyond the final angle positions of the pivot arm housing in a positive and/or a negative direction by a small absolute value, which can for example assume a value of between 1° and 30°, in another example a value of between 2° and 15°, and in a further example a value of approximately 3°.

Further for example, the laser pivot arm and the pivot arm housing each have a separate weight balancing apparatus.

This facilitates a very low-friction weight balancing mechanism that facilitates a movement with little force, i.e., for example, a force of less than 3 N for the laser pivot arm. This precludes a crush from occurring when coupling the patient's eye to the ophthalmological laser therapy system by application of a contact glass or patient interface.

What is essential here is that the separate weight balancing instances are adapted in terms of their properties to their respective function: The weight balance for the laser pivot arm is very precise and low-friction in order to restrict a force on the eye to the aforementioned 3 N. By contrast, the weight balance of the pivot arm housing has more friction and a greater bearing force in the end position to ensure that unwanted deflections of the arm are avoided. Here, it is only necessary to prevent crushing of the entire head, for the purposes of which greater forces are admissible: The maximum admissible force is approximately 65 N in the face. Therefore, a movement with a force of the less than 65 N is facilitated for the pivot arm housing.

Avoiding crushing moreover includes the moment of inertia of the laser pivot arm and the maximum speed of approach to the patient's eye, which emanates from the movement of the patient bearing device, for example a patient couch, or from the movement of the appliance head, having a certain relationship in relation to one another: A moment of inertia of 1.9 $kgm^2$ and a static bearing force of 1.5 N yield a maximum force of ~3 N on the eye in the case of a speed of approach of 30 mm/s. If the moment of inertia is now reduced and assumes value of 1.5 $kgm^2$ for example, then it is possible to slightly increase the maximum speed of approach.

If the weight balance is now produced with the aid of a weight balancing apparatus containing a gas spring, for example, this facilitates a compact construction and the integration of damping for the purposes of avoiding high speeds and for deceleration at the end positions. However, it predominantly comes into question for the weight balance of the pivot arm housing as it is not low-friction on account of the gas seals.

When monitoring the gas spring contained in the weight balancing apparatus, the tension force of the gas spring in the suspension is monitored by virtue of the latter being connected with little movement to a switching element, for example a switch or a photoelectric barrier, and a sensor spring being connected to the suspension, the latter extending up to a stop in the case of a normal force of the gas spring. By contrast, if the force of the gas spring is too low, the sensor spring moves back the suspension of the gas spring and the switching element is opened. If the switching element is in an open position, pivoting down of the laser pivot arm or of the pivot arm housing from a rest position into a work position is not enabled.

Moreover, an ophthalmological laser therapy system, the appliance head of which is also displaceable in the z-direction on the appliance base, is particularly advantageous. This renders it possible to vary the distance between the appliance base and appliance head. As a result of this change in distance, the work height, i.e. the height of the laser exit aperture, is modified in a simple manner. In an example arrangement of the laser source in the appliance head, the laser source is also displaced when displacing the appliance head on the appliance base in the z-direction such that no compensation is required here.

In an example configuration, the ophthalmological laser therapy system comprises a pre-positioning device for pre-positioning of the appliance head.

The arrangement of the pre-positioning device is selected in such a way that an object in a work volume of the laser beam can be observed without parallax when the laser pivot arm is in a work position. Here, the work volume is the possible range of action of the focused laser beam in the case of a laser pivot arm arranged in the work position.

This pre-positioning device for example contains a camera. For the aforementioned reasons, the latter is advantageously affixed to the appliance head. This facilitates fast and simple pre-positioning of the appliance head by the transversal movement in the xy-plane in a y-direction, or if a camera which additionally supplies depth information is used, also in an x-direction and optionally in the z-direction in relation to the appliance base, too.

In a further configuration, the laser pivot arm and/or the pivot arm housing of the ophthalmological laser therapy system contain at least one detection device. Such a detection apparatus serves to capture structures in a work volume of the laser pivot arm. In particular, the detection device can be a video microscope apparatus or an OCT apparatus.

A detection device that is contained on or in the laser pivot arm and/or the pivot arm housing of the ophthalmological laser therapy system renders the use of a conventional surgical microscope, which is usually used in many laser therapy methods in various work steps, optional.

The detection device can be configured as an integrated detection device, i.e. also use the beam guiding structure and, in particular, the laser therapy optical unit of the laser pivot arm. However, the detection device can also be configured as an independent detection device which, at best, likewise emerges through the laser exit aperture and which is directed from there onto a work volume, for example in a tissue of a patient's eye. The same emergence location of laser radiation used for the therapy and detection radiation offers advantages in respect of the calibration of the radiation, in particular in terms of the focuses thereof, in relation to one another.

It is nevertheless also possible to work with a detection device that is part of the laser pivot arm and/or of the pivot arm housing of the ophthalmological laser therapy system, the beam path or wave profile of which, however, is completely independent of that of the laser radiation, for as long as a relationship has been established between the laser radiation and the radiation or the waves employed by the detection device in respect of the use location thereof.

Further examples of detection devices that the laser pivot arm and/or the pivot arm housing can contain are ultrasonic sensors, microwave sensors, an optical coherence tomography (OCT) apparatus, interferometers, wavefront sensors, video sensors or a conventional microscope in a very compact embodiment.

Furthermore, it is advantageous if an input and/or output apparatus is movably fastened to the pivot arm housing of the ophthalmological laser therapy system. In particular, such an input and/or output apparatus can be represented by a therapy screen, with the latter for example being embodied as a touchscreen for input purposes and the output of which being able to be provided in text form and/or graphical form.

In another fundamental example embodiment, the ophthalmological laser therapy system according to the invention is characterized in that, furthermore, an examination pivot arm with an examination device is fastened to the appliance head in a manner pivotable about a second axis. Here, the examination device of the examination pivot arm can also comprise a further therapy option.

The examination pivot arm, too, is pivotable, in particular, between a rest position and a work position. In this embodiment, both the laser pivot arm and the examination pivot arm only have one work position. An examination volume is defined by the examination device and the work position thereof. The laser pivot arm, in turn, determines a work volume of the laser beam, in particular by way of the position of its laser exit aperture in the work position. This work volume describes a volume in which the laser beam emerging out of the laser emergence opening of the laser device is focusable and develops an effect at its focal spot—for example a separating effect or cutting effect in an eye issue by way of photodisruption. Consequently, it is also the volume in which the focal spot of the laser beam can be moved without imaging aberrations or when imaging aberrations are corrected.

Both axes, i.e., the first axis of the laser pivot arm and the second axis of the examination pivot arm, are arranged relative to one another in terms of their relative position such that a work volume of the laser beam, when the laser pivot arm is in a work position, is a partial volume of the examination volume of the examination device on the examination pivot arm, when the latter is in a work position. Here, the partial volume can also be an improper partial volume, i.e. work volume and examination volume are identical.

By contrast, in their respective rest positions, the laser pivot arm is not arranged in the pivot region of the examination pivot arm and the examination pivot arm is not arranged in the pivot region of the laser pivot arm.

In an example embodiment, a second axis of the examination pivot arm is arranged in such a way here that it extends in a non-parallel fashion relative to the first axis of the laser pivot arm. This allows a more compact construction than a system with a second axis extending parallel to the first axis.

Thus, if the ophthalmological therapy system contains a laser pivot arm and an examination pivot arm which are both attached to the appliance head in a pivotable manner then the two pivot arms are two single-axis arm systems, the pivot axes of which are arranged in for example non-parallel and in another example non-perpendicular fashion in relation to one another. Furthermore, the two axes can be arranged lying in a plane. The work position of the examination pivot arm, and hence of the examination device, is derived in this case from the work position of the laser pivot arm and, in particular, the position of the laser exit aperture.

The following regions are presented as examples for the relative position of the second axis, i.e., the pivot axis of the examination pivot arm, in relation to the relative position of the first axis of the laser pivot arm:

an angle of the second axis in relation to a perpendicular plane that extends through the first axis of the laser pivot arm of 0° to 20°, in another example embodiment of 0° to 5°, an angle of the second axis in relation to a horizontal, i.e., level, plane through the first axis of the laser pivot arm of 0° to 50°, in another example embodiment of 20° to 40°, wherein the horizontal plane is a plane that extends parallel to a ground plane on which the ophthalmological laser therapy system is arranged—in a stationary or movable manner.

Furthermore, the second axis for example extends through a point situated at a distance of 200 mm to 400 mm above the axis of rotation of the laser pivot arm, 200 mm to 500 mm behind the laser exit aperture for a laser pivot arm in the work position, i.e., extending toward the appliance head, in the y-direction, and less than 100 mm from the perpendicular plane through the first axis, i.e., the axis of rotation of the laser pivot arm.

The examination pivot arm can also be encompassed by a coaxially mounted examination pivot arm housing, in a fashion analogous to the laser pivot arm with its pivot arm housing. In so doing, the general term pivot arm housing in this case always denotes the housing of the laser pivot arm. Thus, if an examination pivot arm is likewise encompassed by a housing, this is denoted in more detail as an examination pivot arm housing.

Hence, different combinations in respect of the configuration of the two pivot arms are possible for an ophthalmological laser therapy system having a laser pivot arm and an examination pivot arm: The laser pivot arm can be a simple pivot arm that is arranged on the appliance head. However, a laser pivot arm with a pivot arm housing, wherein the laser pivot arm and pivot arm housing are arranged coaxially and separate from one another in a pivotable fashion, is substantially more preferred. This is because for the laser therapy step, in particular, in which a laser exit aperture is coupled to an eye of the patient either by application of a contact glass or a patient interface, or else said laser exit aperture is at least situated in the vicinity of the eye, the advantages of such an "arm-in-arm" solution for the patient safety are significant.

For the examination pivot arm, too, it is possible that either it is arranged as a simple examination pivot arm on the appliance head of the ophthalmological laser therapy system, or else that it is surrounded by an examination pivot arm housing. Here, the decision as to which examination device is encompassed by the examination pivot arm and, if a plurality of examination devices are present, how these or individual elements thereof are arranged in relation to one another is made thereafter. Here, laser pivot arm and examination pivot arm can be used in any combination (both with an arm-in-arm solution, only one of the two with an "arm-in-arm" solution or both as simple pivot arms). This is because, on account of the construction of the arm-in-arm solution, the latter does not require significant additional space and also does not restrict the arrangement of the axes of the two arms in relation to one another.

Depending on the application and, in particular, depending on the examination appliance and the spatial options thereof, it is possible to ensure here that a work position of the laser pivot arm causes a rest position of the examination pivot arm, and vice versa. Optionally, like when using a surgical microscope on the examination pivot arm, for example, this is a safety aspect, and so a prevention of simultaneous work positions of the laser pivot arm with its pivot arm housing and of the examination pivot arm guarantees collision-free work.

The examination pivot arm, too, generally contains a weight balancing apparatus; if an examination pivot arm housing is present, the latter can also have a separate weight balancing apparatus. Thus, here too, a weight balance is obtained which meets the increased safety requirements and nevertheless allows the use of small motors. Here, the arms can be moved manually at all times and with little force outlay.

In this case too, such a weight balancing apparatus can be embodied with a gas spring and corresponding above-described monitoring.

Moreover, naturally, further examination or therapy pivot arms can also be fastened in a pivotable manner on the appliance head of the ophthalmological laser therapy system according to the same principles described here. Here, up to five pivot arms with a dedicated pivot axis in each case are preferably conceivable. These further pivot arms, for which pivoting into different positions requires very different moments of force, then also have corresponding weight balancing apparatuses in each case. If the respective pivot arm comprises a housing, the weight balance thereof is realized with a weight balancing apparatus that is independent from the pivot arm.

Preferably, the examination device of an examination pivot arm of the ophthalmological laser therapy system is a surgical microscope (OPMI). Surgical microscopes are used in corresponding therapy methods on the eye by a large majority of surgeons, particularly in order to observe the course of a therapy method, verify results visually or be able to precisely carry out manual steps contained in the therapy method.

Moreover, an embodiment of the ophthalmological laser therapy system containing an input and/or output apparatus or an examination device, which is characterized in that the input and/or output apparatus is rotatable about an axis that is parallel to the first axis of the pivot arm housing and/or the examination device is rotatable about an axis that is parallel to the second axis of the examination pivot arm, and is coupled by way of a coupling apparatus to the movement of the pivot arm housing or of the examination pivot arm, is of particular interest. By way of example, such a coupling apparatus is a coupling rod or a Bowden cable.

Hence, both the input and/or output apparatus, i.e., a therapy screen, for example, and the examination device, i.e., a surgical microscope, for example, always remain in a work position during a pivot movement of the respective arm on which they are movably fastened. Thus, displays on an input and/or output apparatus are for example always shown in the correct alignment that is preferred by an operator or surgeon; examination devices or components that become damaged or maladjusted during tilting can always be kept in an erect position in this manner, even if the respective pivot arm is in a rest position.

Preferably, the first and/or the second laser therapy optical unit of the ophthalmological laser therapy system contains a scan system with at least two scanners; the movable beam guiding structure is such that the first axis of the laser pivot arm is arranged in the beam axis between the scanners.

As a result, the optical system is insensitive to small twists when pivoting. However, work is only carried out in the work position for safety reasons; i.e., the laser beam is only used for therapeutic treatment, which also includes a surgical treatment in this case, in the work position. In positions other than the work position, there is a risk of the deflection axes of the scanner being significantly twisted in relation to one another.

Furthermore, an advantageous embodiment of the ophthalmological laser therapy system contains a position regulating apparatus for regulating the relative position between the laser pivot arm and/or the examination pivot arm in a work position and a patient's eye. It is configured to reposition the relative position of the appliance head according to position of a patient's eye.

The position regulating apparatus preferably comprises a force sensor and/or a photoelectric barrier. To this end, a force sensor can be arranged in such a way, for example, that the second laser therapy optical unit or the entire laser pivot arm lies on the force sensor when the laser pivot arm is in the work position.

A compression force of the patient's eye against the second laser therapy optical unit or the laser exit aperture, optionally by way of a contact glass or patient interface, unburdens the force sensor. If this is the case, then the position of the appliance head is modified in such a way that the laser pivot arm in the work position moves away from the patient.

By contrast, if a higher compression force is exerted on the force sensor by virtue of the patient's eye pulling on the laser pivot arm in the attached ("docked") state, i.e., for example, in a state connected to the laser exit aperture by way of a contact glass or patient interface, then the position of the appliance head is modified in such a way that the laser pivot arm in the work position approaches the patient's eye. The change in position of the appliance head is brought about by way of an appropriate translational movement relative to the appliance base.

Thus, the regular position regulation is brought about by repositioning the appliance head in the z-direction in a preferred embodiment. In the process, the corresponding work step, in particular the laser therapy step, need not be interrupted. However, if defined lower or upper limit values are obtained in the process, or if movement patterns assessed to be critical are detected, then the method is stopped; i.e., the laser device is optionally switched off. By way of example, this is the case if the patient's eye moves so far down that the attachment of the patient's eye to the laser exit aperture by application of the contact glass or the patient interface can no longer be ensured. By way of example, this is also the case if the patient's eye moves so far or so quickly upward that a compensation by way of repositioning of the appliance head in the z-direction is no longer possible and the laser pivot arm is pivoted upward by a corresponding compression force of the patient's eye; here, the reader is reminded that only a harmless compression force of less than 3 N is required to this end, and so the patient's eye is not injured during the course of this action. If the laser pivot arm is encompassed by a pivot arm housing, then the laser pivot arm is initially "engulfed" in the pivot arm housing with the compression force of less than 3 N, which is harmless to the eye, and so the pivot arm housing then comes to rest on the face. Following this, the pivot arm housing can then be pivoted upwards together with the laser pivot arm with a compression force of less than 65 N, which is harmless to the face.

Such a solution considerably simplifies the construction of a patient couch or, very generally, a patient bearing device, which is used to carry out a laser therapy on a patient's eye, in order to place the patient under the pivot arms of the ophthalmological laser therapy system in the work position. Without such a position regulating apparatus and the safety concept described herein, the patient couch itself would have to react to critical limit values being reached: In addition to the deactivation of the laser therapy system, the movement of the patient couch in the critical direction would also have to be stopped immediately. However, if a position regulating apparatus and the safety concept as described herein are used, it is possible to dispense with such mechanisms on the patient couch: Consequently, the patient couch need no longer be integrated into the ophthalmological laser therapy system or into the functions thereof. Hence, it is possible to use any patient support.

An ophthalmological laser therapy method comprises the following steps:

A patient is positioned on a patient support, preferably on a patient couch, next to an above-described ophthalmological laser therapy system according to the invention, the pivot arms of which are in the rest position. Here, the patient support can have a very simple configuration. It requires no positioning apparatuses, as are otherwise required when the patient has to be brought from a work volume into an examination volume or else into another work volume by way of the position of the patient support. By way of example, it can thus be adjustable in a purely manual fashion.

The appliance head is pre-positioned—for example by the pre-positioning device, for example a camera. To this end, for example, a superposed "symbol", i.e., a predicted position, of the downward pivoted laser pivot arm is made visible on a therapy screen, on which an image produced by the pre-positioning device is displayed. As a result, the appliance head can be pre-positioned laterally in the y-direction, and also in the x-direction and preferably also in the z-direction, i.e. in terms of height, in the case of a camera that supplies depth information.

The laser pivot arm is subsequently pivoted into a work position and further positioned over the patient's eye, for example by application of a video microscope apparatus contained on a pivot arm housing.

The laser therapy step is carried out once the laser pivot arm is positioned over the patient's eye. By way of example, this step can be started by the operator or surgeon by operation of a foot switch.

Once the laser therapy step is complete, the appliance head is preferably initially raised, provided that a corresponding option for displacing the appliance head on the appliance base in the z-direction is provided to this end. Thereupon, the laser pivot arm is pivoted into the rest position.

Optionally, these steps can be repeated over a patient's second eye.

A preferred ophthalmological laser therapy method furthermore includes the following steps:

A pivot arm housing which encompasses the laser pivot arm is pivoted into a work position in synchronous fashion with the laser pivot arm. Here, the laser exit aperture is preferably still retracted into the pivot arm housing.

Prior to the positioning over the patient's eye, the laser pivot arm is pivoted further out of the pivot arm housing. In the process, the second laser therapy optical unit and the laser exit aperture move with a force set by a weight balance of the laser pivot arm.

After performing the laser therapy step, the laser pivot arm is pivoted into the pivot arm housing; i.e., the laser exit aperture is retracted back into the pivot arm housing.

The pivot arm housing is pivoted into the rest position in in a manner synchronous with the laser pivot arm. Here, the weight balance for the laser pivot arm and for the pivot arm housing are preferably carried out independently of one another.

The described ophthalmological laser therapy method can preferably furthermore contain the following steps:

placing a contact glass or a patient interface on the laser exit aperture (9) and securing the contact glass or the patient interface at the laser exit aperture (9) by application of negative pressure, wherein the negative pressure is activated or deactivated by the pressure of the contact glass or the patient interface against the laser exit aperture (9).

suctioning the patient's eye, preferably with assistance by a detection device (13), in particular by a video microscope apparatus, during further positioning of the appliance head (2).

releasing the suction of the contact glass or the patient interface after performing the laser therapy step.

A contact glass or another patient interface is attached to the laser exit aperture by application of negative pressure, wherein the negative pressure is activated or deactivated by the pressure of the contact glass or of the patient interface against the laser exit aperture. As a rule, the contact glass or the patient interface is placed against the laser exit aperture during the still retracted state of the laser pivot arm in this case so that the pressure of the contact glass or patient interface leads to the switching process:

As a rule, the laser pivot arm is never blocked in the extended state for reasons of safety, and so it is always pressed back into the laser pivot arm in the case of pressure in the opposite direction and it consequently has the play necessary for avoiding crushing. However, a resistance is necessary for the switching process.

However, in a special embodiment, such a resistance can also be reached by virtue of the laser pivot arm having a blocking option in the extended option, said blocking option, however, once again being put out of operation by a safety circuit after the application of the contact glass or patient interface and prior to the docking of the contact glass or of the patient interface on the patient's eye such that the laser pivot arm yields to pressure at all times, and retracts, when or after the patient's eye has been docked.

As a result, an attachment of the contact glass or of the patient interface is also possible after pivoting the laser pivot arm out of the pivot arm housing for those ophthalmological laser therapy systems in which the pivot arm housings have a large distance from the laser pivot arm on account of special superstructures and in which attaching the contact glass or the patient interface with a retracted laser pivot arm would be very uncomfortable.

Here, within the meaning of the description, a contact glass is an arched optical element that is, as a rule, adapted to the arching of the cornea of the eye—generally a lens element—or else an optical element that is flat on the side of the eye and usually convexly arched on the side of the laser exit aperture, which lies on the patient's eye and which is intended to establish a fixed relative relationship between the laser exit aperture and the eye of the patient; i.e., it should temporarily affix the patient's eye to the ophthalmological laser therapy system.

A patient interface satisfies the same function. However, the optical element does not rest on the patient's eye in this case. Accordingly, the eye is not deformed by the optical element either. Rather, the patient interface, which generally has a conical form and which is affixed by way of an outer ring—usually by a suction ring—on the eye, is filled with a liquid in which an optical element is immersed with its eye-side surface. As a result, the cornea of the patient's eye is not deformed or only deformed on the outer edge.

The patient's eye is suctioned by further positioning of the appliance head, preferably with assistance by a detection device, in particular a video microscope apparatus. Hence, the patient's eye is now completely affixed to the ophthalmological laser therapy system.

Once performing the laser therapy step has been completed, the suction of the contact glass or of the patient interface is released, for example by virtue of removing the negative pressure.

The described ophthalmological laser therapy method can furthermore advantageously contain the following steps:
planning the treatment parameters on a planning screen (31) prior to placing the patient on the patient support (500), and
performing a transfer to an input and/or output apparatus, in particular a therapy screen (12).

Thus, the treatment parameters are planned on a planning screen prior to the placement of the patient on the patient support and said planning parameters are subsequently transferred to an input and/or output apparatus integrated on the pivot arm housing, i.e., for example, a therapy screen.

Such a therapy screen, which represents an input and output apparatus, is preferably a touchscreen. Here, the therapy screen has a simplified design in relation to the planning screen.

Thus, only a reduced number of parameters, for example, can be presented in the graphical design of the screen, making the therapy screen clearer than the planning screen. This renders it possible to avoid errors within the scope of the ophthalmological laser therapy method.

The described ophthalmological laser therapy method can furthermore contain the following steps:
pivoting an examination pivot arm (14) from a rest position into a work position after pre-positioning the appliance head (1) and/or after pivoting the laser pivot arm (3) from a work position into a rest position after performing the laser therapy step, and
performing further work steps with the aid of an examination device (15).

Not at least, it is very helpful if an examination pivot arm is pivoted from a rest position into a work position after the pre-positioning of the appliance head and/or after pivoting the laser pivot arm from a work position into the rest position after performing the laser therapy step, and if further work steps are performed with the aid of an examination device of the examination pivot arm.

Thus, in its configurations, the solution to the problem according to the invention avoids the disadvantage of repositioning the patient by way of arranging a laser pivot arm, which can be pivoted and positioned over the patient's eye, and optionally arranging a further examination pivot arm, which may contain a surgical microscope as an examination device, for example, in a defined movable arrangement of the two pivot arms in relation to one another. This mobility facilitates alternating positioning of the two pivot arms and hence of the focus of the laser beam and of the surgical microscope, for example, onto the same work point in a work or examination volume (in which the patient's eye is situated), for example for switching between laser therapy and lenticule extraction during a SMILE treatment.

Moreover, the sensitive laser therapy optical unit of the laser pivot arm can be protected by an arm-in-arm principle by use of a coaxially mounted pivot arm housing. Here, laser pivot arm and pivot arm housing are weight-balanced and mounted independently of one another.

In this case, the aforementioned features of the invention, which are explained in various example embodiments, can be used not only in the combinations specified in an example manner but also in other combinations or on their own, without departing from the scope of the present invention.

A description related to device features is analogously applicable to the corresponding method with respect to these features, while method features correspondingly represent functional features of the device described.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 1a to 1d depict an ophthalmological laser therapy system according to the invention, wherein FIG. 1a highlights various portions whose configurations lead to different embodiments of the ophthalmological laser therapy system according to the invention, and FIG. 1b illustrates a standby mode, FIG. 1c illustrates a laser therapy mode and FIG. 1d illustrates an examination mode using a surgical microscope of a first embodiment of a ophthalmological laser therapy system according to the invention.

FIGS. 2a and 2b depict the arm-in-arm principle of a laser pivot arm and pivot arm housing in a preferred embodiment of a ophthalmological laser therapy system according to the invention.

FIG. 5 depict the arrangement of individual elements of an ophthalmological laser therapy system according to the invention in a rest position with a retracted optical unit.

Figure 1B:
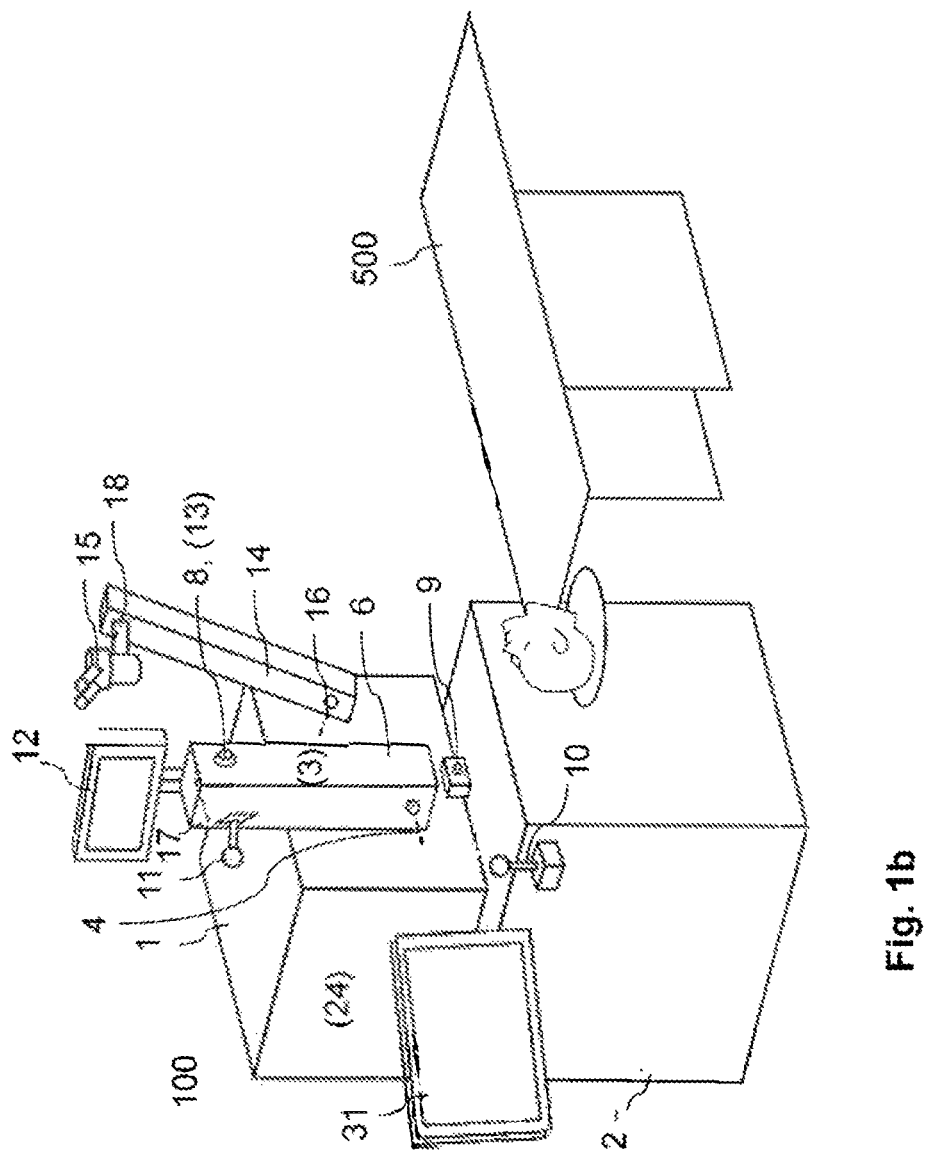

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

FIG. 1a initially highlights various portions that contribute to solving the problem of this invention. Different configurations of these portions lead to various embodiments of the ophthalmological laser therapy system 100 according to the invention.

Initially, it should be noted that the patient couch 500 is not part of the ophthalmological laser therapy system 100 according to the invention; instead, it is only illustrated in the figures to provide an improved understanding of the function and, in particular, the work area of ophthalmological laser therapy systems 100 according to the invention. However, from the function of these ophthalmological laser therapy systems, the advantage of being able to use a very simple embodiment of patient couches 500 at this position becomes comprehensible.

Ophthalmological laser therapy systems 100 according to the invention are distinguished by a laser pivot arm 3 that is fastened to the appliance head 1 in a manner pivotable about a horizontal axis 4 and that can be pivoted back and forth between a rest position and a work position. Since this laser pivot arm 3 is pivoted over the patient for laser therapy on the patient's eye but can be returned into a rest position for steps in which the laser pivot arm 3 is not required in order to use the space above the work position differently, the laser pivot arm 3, firstly, is protected by virtue of the laser pivot arm 3 being enclosed by a pivot arm housing 6, which is fastened in a pivotable manner to the device head 1 in coaxial fashion in relation to the laser pivot arm 3. This is the "arm-in-arm" principle 200. In addition to mechanical protection for the laser pivot arm 3 itself, the "arm-in-arm" principle moreover offers the advantage of independent weight balancing apparatuses for the laser pivot arm 3 and the pivot arm housing 6 and also, in particular, the option of distributing the weights of superstructures. Details of this arm-in-arm principle 200 are shown in FIGS. 2a and 2b.

If use is furthermore made of one or more further independent examination pivot arms 14 in addition to the laser pivot arm 3, said examination pivot arms are each arranged about an axis of pivotable arm systems in relation to one another such that all work steps of a laser therapy on the eye of a patient can be carried out in such a way that the point of action of all work steps aided by the laser pivot arm 3 or one or more examination pivot arms 6 always remains stationary; i.e., the position of the patient's eye need not be changed during the entire laser therapy. The position of the patient's eye in the first work step determines the position of all subsequent work steps and hence the point of action of the devices required in each case, which are on the various pivot arms 3, 14. This is facilitated by a special arrangement 300 of the pivot axes 4, 16 of the various pivot arms 3, 14 in relation to one another on the appliance head 1 of the ophthalmological laser therapy system 100.

Figure 4:
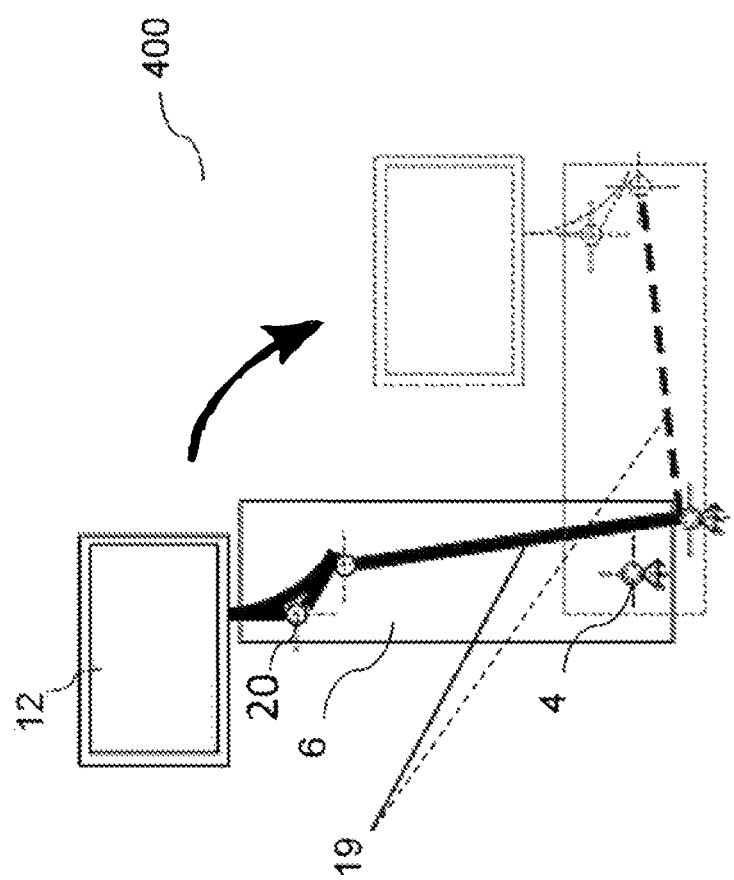
FIG. 4 depict the coupling mechanism of the therapy screen to the movement of the pivot arm housing.

The pivotability of the various arms that can each have superstructures—such as a therapy screen 12 on the pivot arm housing 6 of the laser pivot arm 3 or an examination device 15 on the examination pivot arm 14—leads to a tilt of these superstructures in each case when pivoting the arms from a work position into a rest position, should said superstructures be fastened in an immobile manner. However, these superstructures should nevertheless be usable where applicable. By way of example, even in the rest position, the therapy screen 12 is a screen that is available to a surgeon in the vicinity of the work and should be used, for example, by the surgeon for the display of information or for inputs. Therefore, said screen should be in a non-tilted position, even in the rest position. A similar desire for a non-tilted position even in the rest position may exist for, e.g., a surgical microscope or another examination device, on an examination pivot arm 14, with parts that would be set into unwanted motion in the case of a tilt. This is realized by coupling such superstructures to the respective pivot arm 3, 14 by way of a coupling mechanism 400. FIG. 4 shows a configuration of such a coupling mechanism 400.

These various solution areas, i.e., the "arm-in-arm" principle 200, the arrangement of the pivot axes 300 on the appliance head 1 of an ophthalmological laser therapy system 100 with a laser pivot arm 3 and at least one examination pivot arm 14, and a coupling mechanism 400 for superstructures that should always be present on pivot arms in a non-tilted position, independently of the position of the pivot arms, can be used both together and individually in order to solve the problem of the invention. However, the greatest use is obtained if these different solution areas are used simultaneously.

Figure 1C:
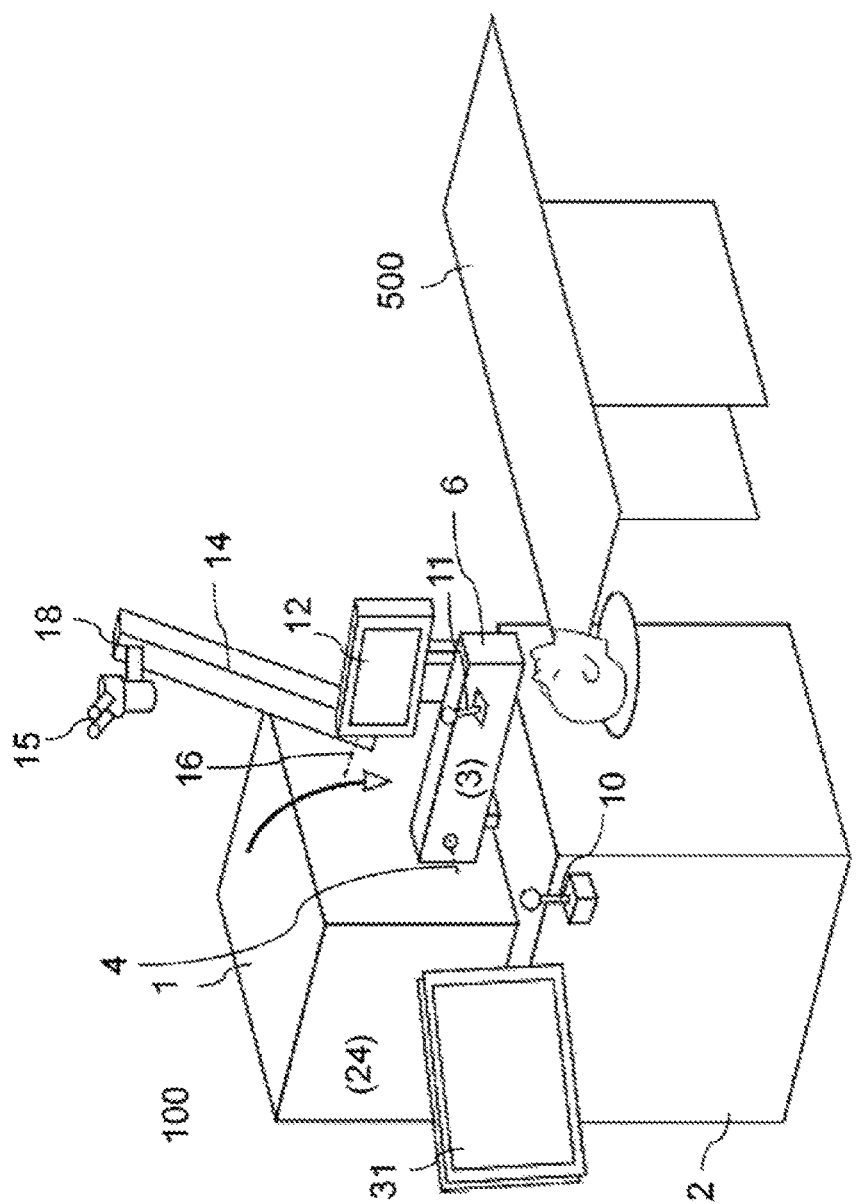
Figure 1D:
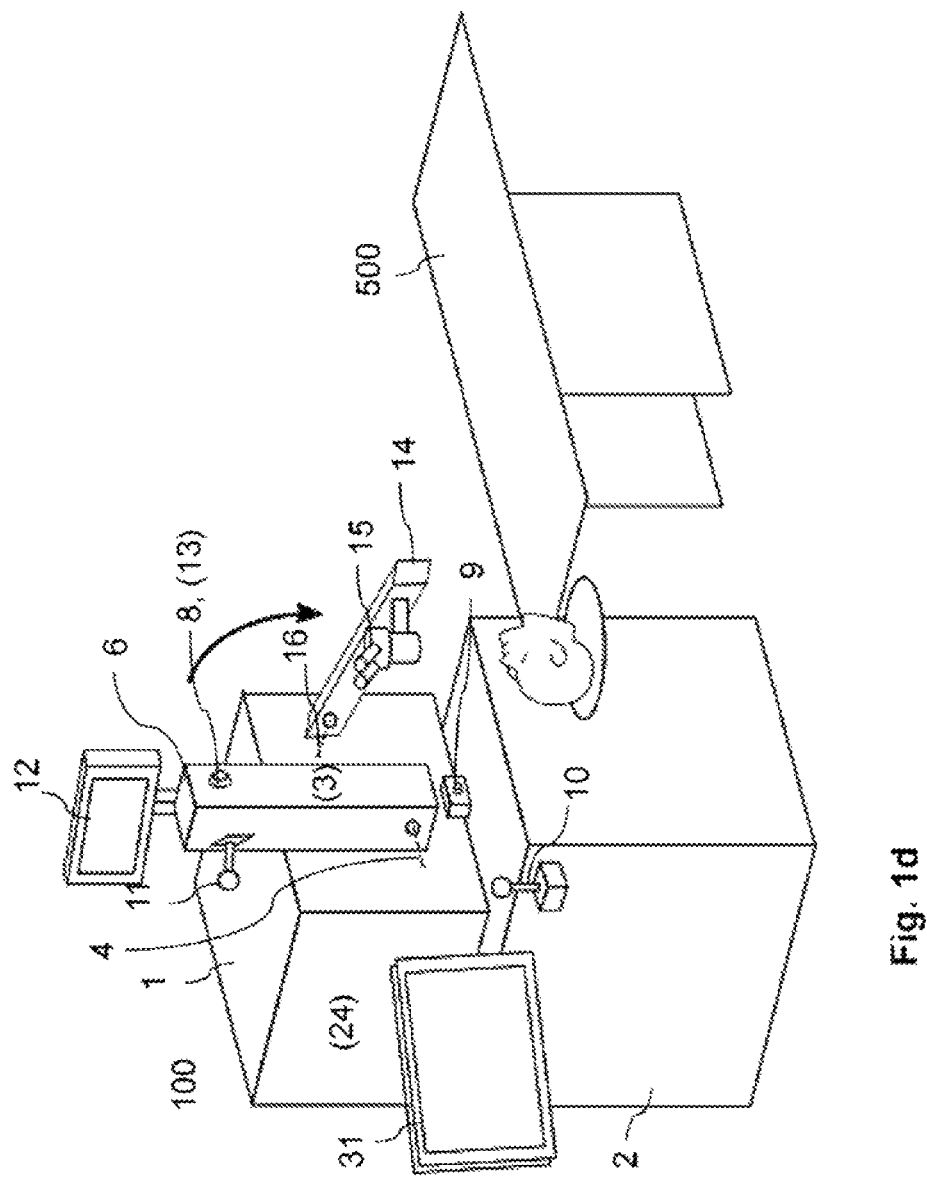

FIGS. 1b-1d now show an exemplary embodiment of an ophthalmological laser therapy system 100 according to the invention for which the "arm-in-arm" principle 200 is realized by a laser pivot arm 3 that is enclosed by a pivot arm housing 6, the ophthalmological laser therapy system 100 contains an additional examination pivot arm 14 with a surgical microscope 15, with the first axis 4 of the laser pivot arm 3 and the second axis 16 of the examination pivot arm 14 on the appliance head 1 having an appropriate arrangement 300 in relation to one another, and a therapy screen 12 movably fastened to the pivot arm housing 6 is coupled to the movement of the pivot arm housing 6 and also a surgical microscope 15 movably fastened to the examination pivot arm 14 is coupled to the movement of the examination pivot arm 14 in such a way that the therapy screen 12 and the surgical microscope 15 are always maintained in a non-tilted manner.

An ophthalmological laser therapy system 100 as shown in this example embodiment can be used very well for a SMILE method, for example, but also for other methods for correcting the visual acuity of an eye or for cataract operations.

Here, FIG. 1b shows a standby mode of this ophthalmological laser therapy system 100, in which all pivot arms 3, 6, 14 are in a rest position, i.e., "parked" pivoted upward on the appliance head 1 in a space-saving manner, and in which, for example, a patient can be appropriately placed and positioned on the patient couch 500.

By contrast, FIG. 1c illustrates a laser therapy mode, i.e., the mode in which the laser pivot arm 3 was brought into a work position. By contrast, the examination pivot arm 14 is still in a rest position.

Finally, FIG. 1d shows an examination mode of the exemplary embodiment of the ophthalmological laser therapy system 100 using a surgical microscope 15. Here, the examination pivot arm 14 has been brought into a work position while the laser pivot arm 3 and its pivot arm housing 6 are in a rest position.

The details should now be specified below.

The exemplary embodiment of the ophthalmological laser therapy system 100 is composed of an appliance base 2 and an appliance head 1 that is adjustable on this appliance base 2 in terms of its height above the ground plane, i.e., the z-direction, and in terms of its position in the plane, i.e., in the x- and y-directions. The device head 1 contains a first part of the laser therapy optical unit required for performing the laser therapy. In the exemplary embodiment, the appliance head 1 also contains the laser source, in this case a femtosecond laser source, required to produce a corresponding pulsed laser beam.

The second part of the laser therapy optical unit is rotatably mounted about a horizontal first axis 4 in a laser pivot arm 3. The laser pivot arm 3 can be pivoted about this first axis 4 from a rest position, in which it projects upward in approximately perpendicular fashion, into a work position, in which it is arranged approximately horizontally on the appliance head 1, i.e., approximately parallel to the ground plane, and back again.

The laser pivot arm 3 with its second laser therapy optical unit and the laser exit aperture 8 is surrounded by a housing, the pivot arm housing 6, in such a way that the pivot arm housing 6 leaves an opening for the laser exit aperture 8. This pivot arm housing 6 is mounted separately to the laser pivot arm 3 in coaxial fashion.

FIGS. 2a and 2b illustrate details of the "arm-in-arm" principle 200 of laser pivot arm 3 and pivot arm housing 6 in one exemplary embodiment of the ophthalmological laser therapy system according to the invention.

Initially, the pivot arm housing 6 pivots by an angle of approximately 90° together with the laser pivot arm 3 between an approximately perpendicular rest position or standby position and a horizontal work position. The movement is restricted by stops.

Overall, the laser pivot arm 3 can be moved by a greater angle than the pivot arm housing 6. Hence, the laser exit aperture 8, on which a contact glass or patient interface for coupling the laser pivot arm 3 to the eye of the patient to be treated can be affixed in a detachable manner, can be positioned protruding out of the pivot arm housing 6 to a greater or lesser extent, or else it can be retracted completely into the pivot arm housing 6.

In the rest position of the laser pivot arm 3 and when pivoting the laser pivot arm 3 and its pivot arm housing 6 from a rest position into a work position and from the work position into a rest position, the laser exit aperture 8 is retracted into the pivot arm housing 6, as illustrated in FIG. 2a. Hence, the laser pivot arm 3 is in a slightly tilted position in comparison with its pivot arm housing 6.

Once the pivot arm housing 6 has arrived in a work position, i.e., in the horizontal, the laser pivot arm 3 is released downward and slightly pivoted further such that it, too, reaches an approximately horizontal position and the laser exit aperture 8 emerges from the pivot arm housing 6. Here, as a consequence of its dedicated weight balancing apparatus 5, the laser pivot arm 3 itself can be moved effortlessly. In the approximately horizontal work position of both pivot arm housing 6 and laser pivot arm 3, as illustrated in FIG. 2b, i.e., with a protruding laser exit aperture 8, the ophthalmological laser therapy system 100 is in the laser therapy mode.

A very low-friction weight balancing apparatus 5 of the laser pivot arm 3 facilitates the movement of the laser pivot arm 3 with a low force F, which is substantially less than 3 N for this exemplary embodiment, and hence a coupling with an eye of a patient to be treated that is secured against crushing: For this example, the force is 1.6+/−0.5 N.

The pivot arm housing 6 is provided with a dedicated weight balancing apparatus 7. The separate coaxial bearing of laser pivot arm 3 and the pivot arm housing 6 surrounding the latter, with separate weight balancing apparatuses 5, 7 and a downwardly secured stop 21 for the pivot arm housing 6, avoids the decisive disadvantage of corresponding systems according to the prior art with pivotable arms, as described in U.S. Pat. No. 8,771,262 B2, for example. No provision is made there for the optical unit to be upwardly deflectable in the work position of the laser pivot arm with a force that is harmless to the eye and independently of external actions, which of course are prevented in the solution according to the invention by the pivot arm housing 6.

The use of separate weight balancing apparatuses 5, 7 for the pivot arm housing 6 and the laser pivot arm 3 has a plurality of advantages.

Motor driven movement or pivoting of the respective arm 3, 6 about the first axis 4 can make do with relatively low-power motors. These substantially only need to overcome the inertia of the system and therefore cannot build up dangerous forces on the pivot arm housing 6.

Moreover, the laser pivot arm 3 and the pivot arm housing 6 can be moved—even together—by hand at all times. This facilitates freeing the patient in the case of a defect or a power outage without problems.

Should the patient couch 500 be moved upward in an unwanted manner, the patient cannot be crushed as the laser pivot arm 3 in its pivot arm housing 6 can be pressed upward with a harmless force.

The weight balancing apparatus 7 of the pivot arm housing 6 contains a gas spring 26. The use of a gas spring 26 has the following advantages: It allows a compact construction of the weight balancing apparatus 7 and can integrate a damping function. The latter protects against speeds that are too high and serves as a brake in the end positions of the pivot movement.

A gas spring 26 has a high friction on account of the gas seals. This is unwanted in the case of the laser pivot arm 3 but wanted in the case of the pivot arm housing 6. It causes the pivot arm housing 6 to stop passively in each position. Thus, for example, the pivot arm housing 6 can also be brought in a motor driven fashion into a type of ready position, where it stops without current and from where it can be brought into the work position manually by the physician. This is advantageous when the physician wishes to exert manual control in relation to the approach of the arm to the patient.

Thus, a gas spring 26 is only seldom used in the weight balancing apparatus 5 of a laser pivot arm 3, while it constitutes a very preferred solution for the weight balancing apparatus 7 of the pivot arm housing 6.

Figure 3A:
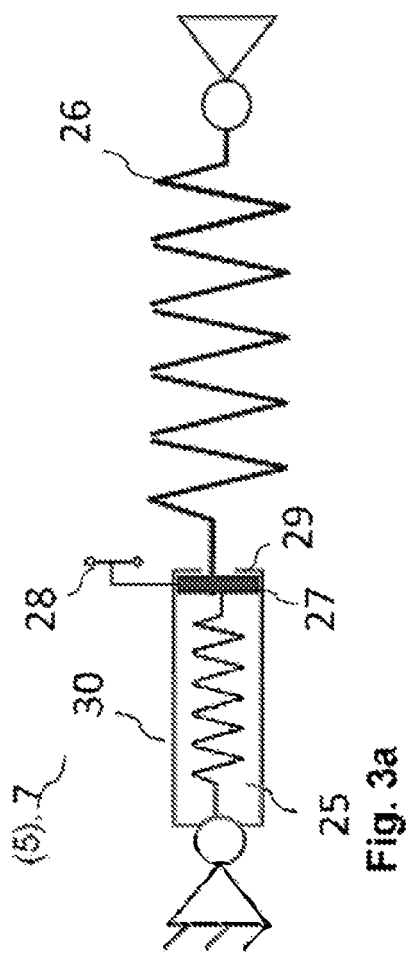
FIGS. 3a and 3b depict a schematic illustration of an apparatus for monitoring the function of the spring of a weight balancing apparatus.
Figure 3B:
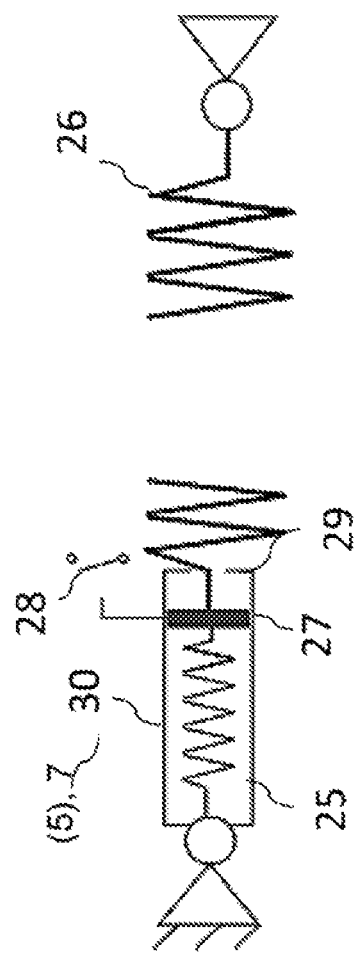

FIGS. 3a and 3b show an apparatus for monitoring the function of the spring of such an example weight balancing apparatus 7, by which a failure of the gas spring 26 can be identified. Here, FIG. 3a illustrates a situation in which the spring force lies in the desired range, while FIG. 3b shows the situation in which the spring force is too low, for example because, as illustrated here, the gas spring 26 is broken. In the latter case—i.e., when there are problems with the gas spring 26—, it is ensured that the downward pivoting of the pivot arm housing 6 is prevented; i.e., the pivot mechanism is blocked.

To this end, the preferred weight balance apparatus 7 contains a gas spring 26, the tension of which in its suspension 27 is monitored. This is effectuated by virtue of the suspension 27 of the gas spring 26 being slightly movable and detachably connected to a switching element 28, which is a pressure switch kept closed by an appropriate pressure in this case. The pivot mechanism of the pivot arm housing 6 is only released in this closed state of the pressure switch. An electromechanically detachable locking mechanism serves to this end.

If the spring force of the gas spring 26 now is sufficiently high, then a sensor spring 25, which is likewise connected to the suspension 27, is extended up to a stop 29 in a guide 30 of the sensor spring 25. Then, the pressure switch 28 is kept closed by the suspension 27 or by an extension of the suspension 27, the locking mechanism is released and the pivot arm housing 6 is pivotable about its pivot axis, i.e., about the first axis 4.

However, if the spring force of the gas spring 26 is too low, i.e., lower than the force of the sensor spring 25, then the sensor spring 25 moves back the suspension 27 of the gas spring 26 in the guide 30. The pressure switch 28 is opened in the process, the locking mechanism remains closed and the pivot mechanism is not released.

FIG. 4 shows a further advantageous aspect of an exemplary embodiment of the ophthalmological laser therapy system 100 according to the invention: Here, the coupling mechanism of the therapy screen 12 to the movement of the pivot arm housing 6 is illustrated as an example of an apparatus 400 coupled to a pivot arm.

The therapy screen 12 is movably fastened to the pivot arm housing 6. In this case, the therapy screen 12, at the same time, is also the screen of a video microscope 13, showing the view from the second laser therapy optical unit and the laser exit aperture 8 onto the eye to be treated. The video image of this video microscope 13, which is displayed on the therapy screen 12, is used by the surgeon, for example for the approach to, and the affixment of a contact glass or another patient interface on, the eye to be treated and for the observation of the laser cuts being carried out.

Further information that is important for the laser therapy progress is likewise displayed on the therapy screen 12. In this exemplary embodiment, the therapy screen 12 is embodied as a touchscreen and consequently also facilitates the input of information or the navigation during the course of the treatment.

The therapy screen 12 is movably fastened to the pivot arm housing 6 in such a way that it is rotatable about an axis 20 that is parallel to the horizontal pivot axis, i.e., the first axis 4, of the pivot arm housing 6. What is achieved by way of a coupling rod 19 is that the therapy screen 12 always remains in the same relative position when pivoting the laser pivot arm 3 together with the pivot arm housing 6. This facilitates the use of the therapy screen 12 both in the rest position and in the work position of the laser pivot arm 3.

As shown further in FIGS. 1b to 1d, the image of a camera 9 serves to pre-position the appliance head 1. Said camera is fastened to the appliance head 1 and therefore has a fixed spatial relation to the position of the appliance head 1. The position is selected in such a way that a largely parallax-free view of the work volume of a therapy laser beam is effectuated, in particular of the possible position of its focus as a work point of a therapy objective in the second laser therapy optical unit.

A graphics that is overlaid on the image of the camera 9 on the therapy screen 12 and/or else on the planning screen 31 already shows in the standby mode, i.e., in the rest position of the laser pivot arm 3, the expected position of the laser pivot arm 3 in its then pivoted-down work position. With the aid of this image, the surgeon can pre-position the appliance head 1 in such a way that the laser pivot arm 3 after pivoting-down into its work position, i.e., in the laser mode, is in an ideal position for the treatment start in respect of an approximate positioning, and only fine positioning in respect of structures of the eye is still necessary.

Furthermore, a joystick 11 for controlling the coupling process to the patient is attached to the pivot arm housing 6. In the work position, the joystick 11, the laser exit aperture 8 of the laser therapy optical unit and the video image of the eye are aligned along a vertical line 23 in order to facilitate an equally ergonomic operation for right-handed and left-handed users.

Moreover, this exemplary embodiment of the ophthalmological laser therapy system 100 according to the invention contains a force sensor which contributes to the automatic position regulation that is important from a safety point of view: To this end, the force sensor is arranged in such a way that the second laser therapy optical unit lies on the force sensor when the laser pivot arm is in the work position.

Pressure of the patient's eye against the second laser therapy optical unit or the laser exit aperture unburdens the force sensor. This leads to an automatic movement of the position of the appliance head 1 in such a way that the laser pivot arm 3 moves away from the patient in the work position. A higher pressure on the force sensor arises by a pull of the patient: As a result of this, the appliance head 1 is then moved in the opposite direction.

FIG. 5 now shows the work space gain as a consequence of the therapy screen 12 remaining non-tilted in the rest position: The space 22 can be used for components of the laser device 24 in the appliance head 1. If the therapy screen 12 were fixedly fastened to the pivot arm housing 6, as illustrated by reference sign 12a, the space 22 would be blocked for the therapy screen 12, pivoting thereto in the rest position, with an additional safety margin.

Now, a typical course of treatment using an above-described ophthalmological laser therapy system 100, as can be used, for example, for a SMILE treatment or as part of a SMILE treatment, is described below:

First, the treatment or therapy parameters are planned on a planning screen 31, which is likewise arranged directly in the ophthalmological laser therapy system 100 in this exemplary embodiment. However, alternatively, the planning screen 31 can also be spatially separated from the ophthalmological laser therapy system 100. When planning, the ophthalmological laser therapy system 100 is preferably in a standby position, i.e., the laser pivot arm 3 and optionally the examination pivot arm 14, too, are pivoted up vertically in the rest position on the system.

The patient is placed on the patient couch 500. This is possible with some comfort on account of the pivoted-up laser pivot arm 3.

Then, the surgeon positions the height of the appliance head 1 by use of a joystick 10 on this appliance head 1, by means of which the translational movement of the appliance head 1 over the appliance base 2 can be controlled. In the process, orientation is provided by the image supplied by the camera 9, said image, including an overlaid symbol of a pivoted-down laser pivot arm 3, being visible on the therapy screen 12 and/or on the planning screen 31. As an alternative to the joystick, the positioning can also be effectuated in other embodiments by inputs on one of the two screens 12, 31 or by way of push-buttons on the laser therapy system 100.

The surgeon triggers the motor-driven pivoting-down of the laser pivot arm 3 in, and together with, its pivot arm housing 6; a corresponding push-button employed to this end is not illustrated in the figures. As a result of the pre-positioning and the still retracted laser exit aperture 8 of the laser pivot arm, a clear space remains between the laser exit aperture 8 and the patient's eye, said clear space expediently having a size of between 50 mm and 150 mm.

Now, a contact glass is placed on the laser exit aperture 8, if this has not yet happened in the rest position of the laser pivot arm 3. The contact glass is held against the laser exit aperture 8 by negative pressure. Activation and deactivation of the hold by negative pressure is carried out in this case by virtue of pressing the contact glass against the laser exit aperture 8; in the process, the latter is still slightly moved in its retracted position and the switching process is triggered. This is advantageous over previously conventional laser therapy systems: There, the hold of the contact glass is switched separately. Consequently, the contact glass may fall down when it is detached. By contrast, in the solution described here, the surgeon or operator always holds sway over the contact glass during the switching process.

Then, the surgeon initiates the release of the movement of the laser pivot arm 3 within the pivot arm housing 6 by use of a joystick rotation of the joystick 11 on the pivot arm housing 6, or alternatively by a separate push-button (not illustrated). An automatic trigger of the movement by way of the applied contact glass is also possible in other embodiments. In the process, the laser exit aperture 8 with the contact glass moves toward the eye with the force set by the weight balancing apparatus 5 of the laser pivot arm 3, which is less than 3 N at the contact glass or level with the laser exit aperture 8. Here, the travel is approximately 50 mm, a range for this travel that is very generally expedient for all ophthalmological laser therapy systems 100 according to the invention is from 30 mm to 100 mm. Hence, a safe distance from the eye, which is approximately 30 mm or, very generally, expediently assumes a value of between 10 mm and 100 mm, still remains.

Finally there is the docking phase, i.e., the phase in which the contact glass is affixed: Here, the surgeon steers the contact glass toward the eye of the patient using the joystick 11 under observation by the video microscope 13. Fixating the eye by suctioning the eye to the contact glass is triggered by a button on the joystick 11 when the correct position is reached. In one configuration, it is possible to assist the correct positioning or centering of the contact glass or another patient interface on the eye by virtue of processing the video microscope image and using this to control the appliance head 1.

Hence, it is now finally possible by use of a foot switch, which is not illustrated here, to start the actual laser therapy step by activating the laser beam, which is guided through the laser therapy optical units and the laser exit aperture and focused in the patient's eye.

After completing this laser therapy step, the suctioning of the eye by application of negative pressure is released by virtue of the pressure being increased here again, the laser pivot arm 3, and hence also the laser exit aperture 8, are pivoted back into the pivot arm housing 6 again and the appliance head 1 is slightly raised by a displacement in the z-direction. Hence, a safe distance from the eye is present once again. If need be, docking could be carried out once again from this position.

However, as a rule, this is not required. The contact glass or the patient interface can be removed from the laser exit aperture 8, with the release being effectuated by brief upward pressure.

Now, the laser pivot arm 3 is pivoted up again together with its pivot arm housing 6; the clear space above the patient is re-established. Now, it is possible to perform further work steps or the patient can leave their position on the patient couch 500. The laser pivot arm 3 with its pivot arm housing 6 pivoting up is initiated electronically, by pushing a button in this case. Alternatively, the laser pivot arm 3 with its pivot arm housing 6 can be pushed manually until this is recognized by a position sensor on the pivot arm housing; following this, a motor takes over the movement.

However, where both eyes of a patient are to be treated, the appliance head 1 can be moved by a translational movement in the x- and/or y-direction over the appliance base 2 prior to pivoting-up of the laser pivot arm 3 with its pivot arm housing 6 in its rest position such that the laser pivot arm 3 with its pivot arm housing 6 is positioned over the other eye. A treatment of the second eye can then be effectuated in the same way by virtue of a new contact glass or patient interface being secured on the laser exit aperture 8 by application of negative pressure, and all steps following this are carried out as described above.

Furthermore, an examination pivot arm 14 containing an examination device, in this case a surgical microscope 15, is also fastened in a pivotable manner about a second axis 16 on the appliance head 1 in this exemplary embodiment of an ophthalmological laser therapy system 100 according to the invention. By way of example, such a surgical microscope is required, or at least suggested, for the second main work step of the "SMILE" treatment. In the present exemplary embodiment, the surgical microscope 15 contains a camera for recording the video and a slit projector for extended observation options in addition to the necessary illumination. However, camera and slit projector also may be lacking entirely at this point or used individually.

The pivot axis of the examination pivot arm 14, i.e., the second axis 16, is positioned at a particularly expedient location in space. This allows bringing the surgical microscope 15 on the examination pivot arm 14 from its rest position in which the examination pivot arm 14 is likewise pivoted up—either in a likewise perpendicular position or in an oblique position—to its work position using only one pivot movement.

This work position is also defined by a restriction of the rotational movement of the examination pivot arm 14 by a stop. Here, it has a special property of coinciding with the work position of the laser pivot arm 3 with its second laser therapy optical unit and its laser exit aperture 8 and hence, according to the invention, this avoids a change in position of the patient during the treatment.

The rest position of the examination pivot arm 14 with its surgical microscope 15 is expediently selected in such a way that the surgical microscope 15 is then situated behind the therapy screen 12. Firstly, this releases the space for the access and exit of the patient and, secondly, facilitates a compact ophthalmological laser therapy system 100 in the standby mode.

In the exemplary embodiment described here, the second axis 16, i.e., the pivot axis of the examination pivot arm 14, is arranged particularly advantageously in relation to the first axis 4, which is the pivot axis of the laser pivot arm 3 and its pivot arm housing 6, in order to be able to embody the ophthalmological laser therapy system 100 as compactly as possible/

The second axis 16 of the examination pivot arm 14 forms an angle in relation to a perpendicular plane through the first axis 4 of the laser pivot arm 3 of 0° and an angle in relation to a horizontal plane through the first axis 4 of the laser pivot arm 3 of 30°.

The second axis 16 extends through a point situated at a distance of 320 mm above the axis of rotation of the laser pivot arm 3, 320 mm behind the work position of the laser exit aperture 8 and 50 mm from the perpendicular plane through the axis of rotation of the laser pivot arm 3.

The surgical microscope 15 has a similar mount on the examination pivot arm 14 as the therapy screen 12 has on the pivot arm housing 6: rotatable about an axis 18 that is parallel to the axis of rotation of the examination pivot arm 14, i.e., the second axis 16, and rotatably connected to the appliance head 1 by a coupling rod 19. Here, the coupling rod 19 has an axis of rotation on the appliance head 1 that is parallel to the first axis 4.

Here, the angle of the first axis 4 in relation to the second axis 16 in space must be compensated in the holder of the surgical microscope 15, i.e., in the relative position of the axis 18, so that the surgical microscope 15 once again stands without tilt in space.

Hence, the surgical microscope 15 remains in its work position in each position of the examination pivot arm 14. This has various advantages:

Movable attachment parts on the surgical microscope 15, such as a slit projector, for example, do not slide out of place. Moreover, the aesthetic appearance is uniform.

Similar to the pivot arm housing 6 of the laser pivot arm 3, the examination pivot arm 14 is also provided with a weight balancing apparatus 7 containing a gas spring 25. Here too, this again has the advantages already described above: The use of a weak motor for moving the examination pivot arm 14, rendered possible thereby, offers safety in relation to a risk of crushing the patient's head. The corresponding configuration of the drive can be kept relatively small and it is more cost-effective than a solution that has to balance the entire weight. Moreover, the examination pivot arm 14 is also movable by hand at all times.

In the case of an examination pivot arm 14, which contains a surgical microscope 15 or else other superstructures which are not provided for contact with the eye, i.e., which do not contain any protruding optical units or the like, the risk of crushing a patient's head is decisive in this case, and it is possible to work with the maximum forces or smaller forces on the patient's head of less than 65 N—as described above. However, in other embodiments, in which an examination device 15 requires contact with the eye, it is once again necessary to apply the "arm-in-arm" principle and consequently it is necessary to avoid a risk of crushing the eye by the inner pivot arm in this case, said inner pivot arm containing the eye-contacting examination device 15, by virtue of working with substantially lower maximum forces of less than 3 N on the eye—as described above.

If such an examination pivot arm 14 with a surgical microscope 15 is present, it is possible to perform the complete SMILE treatment using the ophthalmological laser therapy system 100 according to the invention. To this end, after pivoting up the laser pivot arm 3 with its pivot arm housing 6 into its rest position after completing the actual laser therapy step, as described here, the treatment is continued as follows:

The surgeon initiates the motor-driven downward pivoting of the examination pivot arm 14 by pressing a button. The motor moves the examination pivot arm 14 into its work position, where it rests on a stop. The work position is determined by expedient selection of the relative position of the two pivot axes, i.e., the first axis 4 and the second axis 16, and the end position of the examination pivot arm 14 determined by the stop is determined in such a way that the eye to be treated further lies in the examination volume of the surgical microscope 15 directly after pivoting down the examination pivot arm 14.

Minor corrections, to the extent that these are necessary, are possible by adjusting the position of the appliance head 1 in relation to the appliance base 2 by translational movements. Serving to this end is the joystick 10 present on the appliance base 2, a separate foot console or a joystick present on the surgical microscope 15.

Once examination pivot arm 14 with the surgical microscope 15 has been positioned accordingly, the lenticule extraction is carried out by the surgeon.

After completing the lenticule extraction, the examination pivot arm 14 with the surgical microscope 50 is pivoted up in a motor-driven manner and consequently pivoted back into its rest position. This can be initiated by pressing a button or else—as already described above for the pivot arm housing 6 and the laser pivot arm 3—by pushing. Hence, the clear space over the patient is re-established.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An ophthalmological laser therapy system comprising:
an appliance base,
an appliance head, a laser device including a laser source, a first laser therapy optical unit and a laser pivot arm with a second laser therapy optical unit and a laser exit aperture,
wherein
the appliance head is displaceable on the appliance base in an x-y-plane by a translational movement,
the laser pivot arm is coupled to the appliance head to be pivotable about a first axis; and
the ophthalmological laser therapy system further comprising a pre-positioning device that pre-positions the appliance head.

2. The ophthalmological laser therapy system as claimed in claim 1, wherein the laser pivot arm is coupled to the appliance head to be pivotable about the first axis between a laser rest position and a laser work position.

3. The ophthalmological laser therapy system as claimed in claim 2, wherein the arrangement of the pre-positioning device is selected in such a way that an object in a work volume of a laser beam exiting the laser exit aperture of the laser pivot arm can be observed without parallax when the laser pivot arm is in the laser work position.

4. The ophthalmological laser therapy system as claimed in claim 1, wherein said pre-positioning device includes a camera.

5. The ophthalmological laser therapy system as claimed in claim 4, wherein the camera of the pre-positioning device is affixed to the appliance head.

6. The ophthalmological laser therapy system as claimed in claim 5, wherein the camera additionally is configured to supply depth information.

7. The ophthalmological laser therapy system as claimed in claim 1, further comprising an examination pivot arm with an examination device, which movably defines an examination volume and is fastened to the appliance head to be pivotable about a second axis, and wherein both the first axis and the second axis are arranged relative to one another in terms of relative position such that a work volume of a laser beam, when the laser pivot arm is in the laser work position, is a partial volume of the examination volume of the examination device on the examination pivot arm, when the examination pivot arm is in an examination work position, while the laser pivot arm and the examination pivot arm are not arranged in the pivot region of the respective other pivot arm when the laser pivot arm and the examination pivot arm are in respective laser rest position and examination rest position.

8. The ophthalmological laser therapy system as claimed in claim 7, wherein the second axis of the examination pivot arm extends to be non-parallel relative to the first axis of the laser pivot arm.

9. A method for pre-positioning an ophthalmological laser therapy system, comprising:
placing a patient onto a patient support adjacent an ophthalmological laser therapy system comprising:
an appliance base,
an appliance head,
a laser device that includes a laser source, a first laser therapy optical unit and a laser pivot arm with a second laser therapy optical unit and a laser exit aperture,
wherein
the appliance head is displaceable on the appliance base in an x-y-plane by a translational movement and the laser pivot arm is coupled to the appliance head in a manner pivotable about a first axis between a laser rest position and a laser work position,
wherein, when the laser pivot arm is in the rest position, the method further comprises:
pre-positioning the appliance head by application of a pre-positioning device, such that the laser pivot arm after pivoting-down into the work position is in an ideal position for a laser treatment start in respect of an approximate positioning, and only fine positioning in respect of structures of the eye is still necessary.

10. The method for pre-positioning an ophthalmological laser therapy system as claimed in claim 9, further comprising pre-positioning a camera in association with the appliance head.

11. The method for pre-positioning an ophthalmological laser therapy system as claimed in claim 9, further comprising making visible a superposed predicted position of a downward pivoted laser pivot arm on a therapy screen, on which an image produced by the pre-positioning device is displayed.

12. The method for pre-positioning an ophthalmological laser therapy system as claimed in claim 11, further comprising pre-positioning the appliance head laterally in a y-direction.

13. The method for pre-positioning an ophthalmological laser therapy system as claimed in claim 12, further comprising pre-positioning a height of the appliance head in a z-direction, in relation to the appliance base.

14. The method for pre-positioning an ophthalmological laser therapy system as claimed in claim 12, further comprising supplying depth information via the pre-positioning device and pre-positioning the appliance head laterally in an x-direction.

15. The method for pre-positioning an ophthalmological laser therapy system as claimed in claim 9, the method further comprising:
subsequently pivoting the laser pivot arm into the laser work position and further positioning the laser pivot arm over the patient's eye by application of a video microscope apparatus contained on a pivot arm housing.

16. The method for pre-positioning an ophthalmological laser therapy system as claimed in claim 15, further comprising maintaining a clear space between the laser exit aperture of the laser pivot arm while the laser exit aperture is in a retracted position and the patient's eye as a result of the pre-positioning.

17. The method for pre-positioning an ophthalmological laser therapy system as claimed in claim 16, further comprising making the clear space have a size of between 50 mm and 150 mm.

18. The method for pre-positioning an ophthalmological laser therapy system as claimed in claim 9, the method further comprising:
pivoting an examination pivot arm from an examination rest position into an examination work position after pre-positioning the appliance head and/or after pivoting the laser pivot arm from the laser work position into the laser rest position after performing the laser therapy step for performing further work steps with the aid of an examination device.

* * * * *

UNITED STATES PATENT AND TRADEMARK OFFICE
CERTIFICATE OF CORRECTION

| | |
|---|---|
| PATENT NO. | : 12,070,423 B2 |
| APPLICATION NO. | : 17/369870 |
| DATED | : August 27, 2024 |
| INVENTOR(S) | : Karsten Festag |

Page 1 of 1

It is certified that error appears in the above-identified patent and that said Letters Patent is hereby corrected as shown below:

In the Specification

Column 1, Line 7, delete "2018," and insert -- 2018, now U.S. Pat. No. 11,071,649, --

Column 12, Line 21, delete "in a" and insert -- a --

Column 14, Line 59, delete "depict" and insert -- depicts --

Column 14, Line 61, delete "depict" and insert -- depicts --

Column 22, Line 59, delete "possible/" and insert -- possible. --

In the Claims

Column 25, Line 8, in Claim 1, delete "axis; and" and insert -- axis, and --

Column 25, Line 63, in Claim 9, delete "movement and" and insert -- movement, and --

Signed and Sealed this
Twenty-fourth Day of December, 2024

Derrick Brent
*Acting Director of the United States Patent and Trademark Office*